United States Patent [19]

Winkley et al.

[11] Patent Number: 4,935,515

[45] Date of Patent: Jun. 19, 1990

[54] 2,3,4,5-TETRAHYDRO-1H-[1,2,5]TRIAZOCINO(1,2-A)[1,2,4]BENZO-TRIAZIN-7(8H)-ONES, THIONES AND DERIVATIVES

[75] Inventors: Michael W. Winkley, Malvern; James L. Diebold, Norristown, both of Pa.

[73] Assignee: American home Products Corporation, New York, N.Y.

[21] Appl. No.: 432,245

[22] Filed: Nov. 6, 1989

Related U.S. Application Data

[62] Division of Ser. No. 159,623, Feb. 23, 1988, Pat. No. 4,882,323.

[51] Int. Cl.$^5$ ............................................. C07D 487/02
[52] U.S. Cl. .................................................... 540/554
[58] Field of Search .......................................... 540/554

[56] References Cited

U.S. PATENT DOCUMENTS 4,801,706 1/1989 Winkley et al. ..................... 540/554

Primary Examiner—Mary C. Lee
Assistant Examiner—Robert C. Whittenbaugh
Attorney, Agent, or Firm—Arthur G. Seifert

[57] ABSTRACT

Disclosed herein are novel 1,2,3,4,5,6-hexahydro[1,3,6]-triazocino[1,2-a]benzimidazole of Formulas I and II:

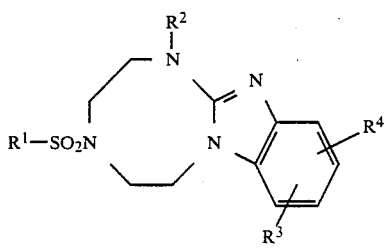

Formula I

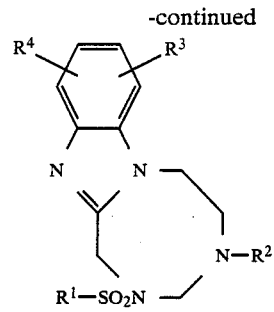

Formula II wherein
$R^1$ may be phenyl, m- or p-nitrophenyl, m- or p-methylsulfonylaminophenyl, napthtyl, naphthyl mono-substituted by nitro or methylsulfonylamino, benzofurazanyl, 2-pyrimidinyl, 2- or 4-pyridinyl, 2- or 4-naphthyridinyl, pyrazinyl, isoquinolinyl, or quinolinyl;

$R^2$ may be hydrogen; $C_1$-$C_8$ alkyl; phenyl($C_1$-$C_4$)alkyl or substituted-phenyl($C_1$-$C_4$)alkyl, in which phenyl may have one to three substituents selected from $C_1$-$C_4$ alkyl, $C_1$-$C_4$ alkoxy, fluorine, chlorine or bromine; phenyl or substituted-phenyl in which the phenyl substituents are the same as for substituted-phenyl ($C_1$-$C_4$)alkyl; 2- or 4-pyrimidinyl; pyrazinyl; imidazolyl; $C_1$-$C_4$ alkanoyl; halo or dihalo-($C_1$-$C_4$)alkanoyl, in which halo is fluoro or chloro; benzoyl or benzoyl substituted on the phenyl ring by one or two $C_1$-$C_4$ alkyl groups; $C_1$-$C_4$ alkanoyloxy; $C_1$-$C_4$ alkylamino($C_1$-$C_4$alkanoyl; $C_1$-$C_4$ alkyloxycarbonyl; $C_1$-$C_4$ alkylaminocarbonyl; phenylaminocarbonyl in which phenyl may have one to three $C_1$-$C_4$ alkyl groups; phenyloxy or naphthyloxy-($C_1$-$C_4$)alkyl in which the phenyl or naphthyl ring may be substituted by one to three $C_1$-$C_4$ alkyl groups; $C_1$-$C_4$ alkylsulfonyl; ($C_1$-$C_4$)alkyl- or N-di-($C_1$-$C_4$ alkyl)carboxamido($C_1$-$C_4$)alkyl; N-phenyl or substituted phenylcarboxamido-($C_1$-$C_4$)alkyl in which phenyl may be substituted as above for $C_1$-$C_4$ alkyl-substituted phenyl; cyano; amidino in which each N atom is substituted by a $C_1$-$C_4$ alkyl group; and $C_1$-$C_4$ alkylguanidino; and $R^3$ and $R^4$ are, independently, selected from hydrogen, $C_1$-$C_4$ alkyl, $C_1$-$C_4$ alkoxy, fluorine and chlorine, or acid addition salts thereof. Compounds of formulas I and II having certain values of $R^2$ are antiarrhythmic or antiischaemic agents. The remaining values of $R^2$ provide intermediate compounds of formulas I and II.

Also disclosed herein a novel tetrahydro-3-substituted-7-substituted-1H[1,2,5]triazepino[1,2-a][1,2,4]benzotriazines, wherein the 7 substituent may be —SMe, —Cl or Br and the 3 substituent is the same as $R^2$ in formulas I and II above. These compounds also serve as intermediates for the production of the antiarrhythmic agents for formula II above.

13 Claims, No Drawings

2,3,4,5-TETRAHYDRO-1H-[1,2,5]TRIAZOCINO(1,2-A)[1,2,4]BENZOTRIAZIN-7(8H)-ONES, THIONES AND DERIVATIVES

This application is a division of copending U.S. application Ser. No. 07/159,623, filed on Feb. 23, 1988, now U.S. Pat. No. 4,882,323, issued on Nov. 21, 1989.

BACKGROUND OF THE INVENTION

Class III anti-arrhythmic agents may be categorized as having the ability to markedly prolong cardiac action potential duration without producing significant changes in maximal upstroke velocity. Unlike Class I anti-arrhythmic agents, a pure Class III agent displays no effects on cardiac sodium channels. The electrophysiologic properties of a compound defining a Class III activity profile are observed in vivo as negligible effects on atrial, ventricular and H-V conduction time while producing a marked increase (greater than 20 percent) in both the atrial and ventricular refractory period. In contrast, Class I agents will demonstrate a marked slowing of ventricular conduction velocity without significant changes in ventricular refractory period. Recent reviews of these agents are by Bexton et al., Pharmacology and Therapeutics, 17, 315–55 (1982); Vaughon-Williams, Journal of Clinical Pharmacology, 24, 129–47 (1984) and Thomis et al., Annual Report of Medicinal Chemistry 18, 99–108 (1983).

DETAILED DESCRIPTION OF THE INVENTION

In its first aspect, this invention provides 1,2,3,4,5,6-hexahydro[1,3,6]triazocino[1,2-a]benzimidazole of Formulas I and II:

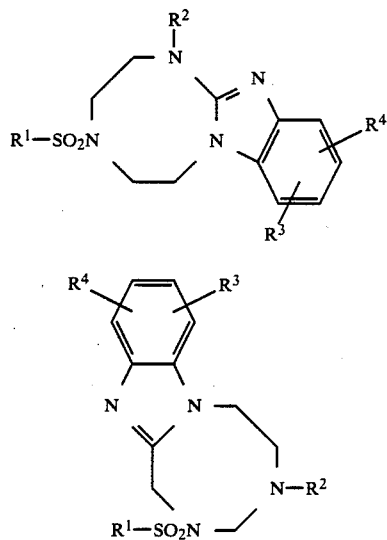

Formula I

Formula II wherein $R^1$ may be phenyl, m- or p-nitrophenyl, m- or p-methylsulfonylaminophenyl, naphthyl, naphthyl monosubstituted by nitro or methylsulfonylamino, benzofurazanyl, 2-pyrimidinyl, 2- or 4-pyridinyl, 2- or 4-naphthyridinyl, pyrazinyl, isoquinolinyl, or quinolinyl;

$R^2$ may be hydrogen; $C_1$–$C_8$ alkyl; phenyl($C_1$–$C_4$)alkyl or substituted-phenyl($C_1$–$C_4$)alkyl, in which phenyl may have one to three substituents selected from $C_1$–$C_4$ alkyl, $C_1$–$C_4$ alkoxy, fluorine, chlorine or bromine; phenyl or substituted-phenyl in which the phenyl substituents are the same as for $C_1$–$C_4$ alkyl-substituted-phenyl; 2- or 4-pyrimidinyl; pyrazinyl; imidazolyl; $C_1$–$C_4$ alkanoyl; halo or dihalo-($C_1$–$C_4$)alkanoyl, in which halo is fluoro or chloro; benzoyl or benzoyl substituted on the phenyl ring by one or two $C_1$–$C_4$ alkyl groups; $C_1$–$C_4$ alkanoyloxy; $C_1$–$C_4$ alkylamino($C_1$–$C_4$)alkanoyl; $C_1$–$C_4$ alkyloxycarbonyl; $C_1$–$C_4$ alkylaminocarbonyl; phenylaminocarbonyl in which phenyl may have one to three $C_1$–$C_4$ alkyl groups; phenyloxy or naphthyloxy-($C_1$–$C_4$)alkyl in which the phenyl or naphthyl ring may be substituted by one to three $C_1$–$C_4$ alkyl groups; $C_1$–$C_4$ alkylsulfonyl; N-($C_1$–$C_4$)alkyl- or N-di-($C_1$–$C_4$alkyl)carboxamido($C_1$–$C_4$)alkyl; N-phenyl or substituted phenyl-carboxamido-($C_1$–$C_4$)alkyl in which phenyl may be substituted as above for substituted-phenyl($C_1$–$C_4$)alkyl; cyano; amidino in which each N atom is substituted by a $C_1$–$C_4$ alkyl group; and $C_1$–$C_4$ alkylguanidino; and $R^3$ and $R^4$ are, independently, selected from hydrogen, $C_1$–$C_4$ alkyl, $C_1$–$C_4$ alkoxy, fluorine and chlorine, or acid addition salts thereof.

The compounds of Formula I and II, and their non-toxic, pharmaceutically acceptable addition salts, with the following values for $R^1$, $R^2$, $R^3$ and $R^4$ (as fully defined above) exhibit properties as antiarrhythmic agents: $R^1$ is as defined above; $R^2$ is hydrogen, $C_1$–$C_8$ alkyl, phenyl($C_1$–$C_4$)alkyl, substituted-phenyl($C_1$–$C_4$)alkyl, phenyl, substituted-phenyl, 2 or 4-pyrimidinyl, pyrazinyl, imidazolyl, halo or dihalo-($C_1$–$C_4$)-alkanol, substituted-benzoyl, $C_1$–$C_4$alkylamino($C_1$–$C_4$)alkanoyl, phenyloxy or naphthyloxy($C_1$–$C_4$)alkyl, ($C_1$–$C_4$)alkylsulfonyl, N-($C_1$–$C_4$)alkyl or N-di-($C_1$–$C_4$alkyl)carboxamido($C_1$–$C_4$)alkyl, N-phenyl or substituted phenylcarboxamido($C_1$–$C_4$)alkyl, and $C_1$–$C_4$alkylguanidino; and $R^3$ and $R^4$ are as defined above. Preferred values for $R^1$ are m- or p-nitrophenyl, m- or p-methylsulfonylaminophenyl and benzofurazanyl. Most preferred values of $R^1$ are p-nitrophenyl and m- or p-methylsulfonylaminophenyl. Preferred values of $R^2$ are hydrogen, $C_1$–$C_6$ alkyl, $C_1$–$C_4$ alkylphenyl, substituted-phenyl($C_1$–$C_4$)alkyl, in which phenyl may have one or two $C_1$–$C_4$ alkyl or chloro substituents, 4-pyrimidinyl, $C_1$–$C_4$alkylamino($C_1$–$C_4$)alkanoyl, ($C_1$–$C_4$)alkylbenzoyl, phenyloxy($C_1$–$C_4$)alkyl, N-di-($C_1$–$C_4$alkyl)carboxamido($C_1$–$C_4$)alkyl, N-phenyl or substituted-phenylcarboxamido ($C_1$–$C_4$) alkyl, and $C_1$–$C_4$ alkylguanidino. Most preferred values of $R^2$ are hydrogen, $C_1$–$C_4$ alkyl, benzyl, phenyl, 4-pyrimidinyl, (N-dimethyl or diethyl)-carboxamidomethyl or ethyl, N-(2,6-dichlorophenyl)-carboxamidomethyl or ethyl, N-(2,6-dimethylphenyl)aminocarbonyl, and ethylguanidino. $R^2$ is hydrogen is particularly preferred with respect to Class III antiarrhythmic properties.

Preferred values of $R^3$ and $R^4$ are, independently, hydrogen, methyl and ethyl. Most preferred values of $R^3$ and $R^4$ are hydrogen.

Compounds of Formulas I and II having values of $R^2$ other than those described above with respect to antiarrhythmic properties serve as intermediates in the preparation of such pharmacologically active compounds. Preferred values of $R^2$ for such intermediate compounds are phenyl or substituted phenyl, $C_1$–$C_4$ alkanoyl, $C_1$–$C_4$ alkanoyloxy, and $C_1$–$C_4$ alkyloxycarbonyl. $R^2$ is phenyl is particularly preferred as a protective group on such intermediate compounds. For such intermediate compounds of Formula II, SO$_2$R$_1$ may also be replaced by hydrogen or a benzoyl or cyano group.

Further novel intermediate compounds and chemical processes, for which patent protection is also sought, are described below in the description of alternate methods for preparing the compounds of Formulas I and II of the invention.

A standard pharmacological procedure used to determine anti-arrhythmic activity in standard experimental animals is as follows:

Rats weighing between 400–500 gms are anesthetized with 35–40 mg/kg sodium pentobarbital intraperitoneally. Rats are close-clipped on the neck and left thorax prior to cannulation of the jugular vein and carotid artery for measurement of arterial blood pressure and injection of drug. A tracheotomy is performed and respiration provided by a Harvard Model 681 respirator at a rate of approximately 55 cycles/min and a volume of 4 cc per cycle. The rat is then placed upon its right side and the heart is exposed by making an incision and separating the ribs. 4-0 Silk on taper R-B-1 needle is making an incision and separating the ribs. 4-0 Silk on taper R-B-1 needle is passed under the left anterior descending coronary artery (LAD) at a location just under the tip of the left atrial appendage. The suture is left to be tied upon occlusion.

The subject rat is allowed to stabilize for 5 to 15 minutes before the administration of drug as a bolus via the cannulated jugular vein. The total drug dose volume is kept constant between 0.20–0.25 ml. Fifteen minutes after dosing, the LAD is occluded by tying the suture. This procedure provokes severe ventricular arrhythmia, terminating in ventricular fibrillation and death in at least about 65 percent of animals given vehicle only. The development and progression of ventricular arrhythmia is monitored for a period of 20 minutes. Lead II ECG and cardiotachometer output are recorded on a Beckman R612 recorder.

Mean arterial pressure (MAP) is monitored throughout the experiment and the following values recorded: (1) MAP prior to drug, (2) maximal change in MAP following drug and before LAD occlusion, and (3) MAP just prior to LAD occlusion. Changes in cardiac electrical activity are determined from the Lead II electrocardiogram. The dysrhythmias are scored as follows: (1) normal sinus rhythm, (2) isolated premature ventricular complexes, (3) nonsustained ventricular tachycardia (repetitive beats of ventricular origin lasting &15 sec.), (4) sustained ventricular tachycardia (repetitive ventricular activity lasting §15 sec.), (5) self-terminating or reversible ventricular fibrillation (VF rev), and (6) irreversible VF (VF irrev. death). The incidence of death in the drug-treated group is then compared to that in the untreated control group (generally §65%). Five animals are included in each drug group.

Arrhythmia scores are calculated for each group of animals for purposes of obtaining more quantitative rankings for anti-arrhythmic efficacy. The equation, $$\sum_{n=1}^{i} A \times AS$$

is used, where A=fraction of animals with a certain kind of arrhythmias (e.g., ventricular fibrillation, sustained ventricular tachycardia) and AS is the arbitrary score assigned to that arrhythmia:

|     | A                                    | AS  |
| --- | ------------------------------------ | --- |
| (a) | no arrhythmia                        | −5  |
| (b) | isolated premature beats (PVC's)     | +5  |
| (c) | non-sustained ventricular tachycardia| +10 |
| (d) | sustained ventricular tachycardia    | +20 |
| (e) | reversible ventricular fibrillation  | +40 |
| (f) | death                                | +50 |

Thus, for the purpose of these coronary ligation (C.L.) experiments, a score from −5 (no arrhythmia) to 50 (death) is assigned to the response of each rat in a test group, based upon the number, type and severity of each response. The sum of the percent of animals at each response level times the point score assigned to that response level equals the score value of the compound being tested. The lower the score, the more active the compound in preventing ventricular dysrhythmia.

Anti-arrhythmic activity may be determined or further characterized, particularly to differentiate between Class I and Class III activity, in accordance with the following standard pharmacological procedure:

Bundles of free-running Purkinje fibers with attached myocardium obtained from either ventricle of adult dog heart are pinned without stretching to the bottom of a 10 ml tissue chamber and continuously superfused with oxygenated Tyrode's solution at a flow rate of 10 ml/min. The composition of the Tyrode's solution is (mM); NaCl 150; KCl: 4.0; CaCl$_2$ 2.7; MgCl$_2$ 0.5; HEPE buffer (7.4) 10; dextrose 5.5. The solution was aerated with 100% O$_2$. Bath temperature is maintained at 36±0.5° C. by circulating the superfusate through a thermostatically controlled water bath immediately prior to entering the tissue chamber.

Preparations are stimulated through bipolar Teflon-coated platinum wires, bared at the tips, placed on the endocardial surface of the attached myocardium using a W.P.I. digital stimulator set to deliver constant current pulses 1–2 msec in duration at cycle lengths (c.l.) of 330 or 1000 msec. Stimulus strength is set at approximately 2×diastolic threshold, and adjusted as required throughout the experiment. All preparations are allowed to equilibrate in the tissue chamber for at least 1 hour before measurements are begun. Subsequently, a minimum of 60 minutes is allowed for equilibration with each drug-containing superfusate before post-drug measurements are made. Impalements are made at 6–10 sites throughout the preparation before and after drug exposure. Offset potentials are re-checked at the conclusion of each experiment.

Glass microelectrodes filled with 3M KCl are coupled to high impedance negative capacitance electrometers (W. P. Instruments, New Haven, CT), and Ag-/AgCl half-cells used as reference electrodes. The first derivative of the action potential upstroke (V$_{max}$) is obtained using an analog differentiator circuit, coupled to a peak-hold circuit that retained the recorded value of V$_{max}$ for 30–70 msec. Action potential and V$_{max}$ tracings are displayed on a Tektronix storage oscilloscope, and photographed for later analysis. In addition chart paper recordings of V$_{max}$ were obtained using the peak-hold device output.

Fresh stock solutions of drug are prepared for each experiment. Compounds are dissolved in distilled water at total concentrations of 1–10 mg/ml, and subsequently diluted to a final concentration of 3 $M in appropriate volumes of normal Tyrode's solution for evaluation.

Action potential (AP) parameters measured included: diastolic take-off potential (or activation voltage, $V_{as}$); AP overshoot ($V_{as}$); AP duration measured as the time taken to repolarized to $-20$ mV ($APD_{20}$), $-60$ mVL ($APD_{60}$), and $-80$ mV ($APD_{80}$); and maximal upstroke velocity ($V_{max}$). Data are compared using a two-sample t-test, with statistical significance taken as p&0.05. An increase in $APD_{60}$ that occurred without a significant change in $V_{max}$ is taken, by definition, to indicate Class III anti-arrhythmic activity.

The data obtained from these experiments establish the compounds of this invention described above as useful Class III anti-arrhythmic agents. Thus, when tested according to this procedure, the compound of Example 7, 1,2,3,4,5,6-hexahydro-4-[(4-nitrophenyl)sulfonyl][1,3,6]triazocino[1,2-a]benzimidazole, hydrochloride had % $ADP_{60}=+8$ and % $V_{max}=+3$. The compound of Example 8, N-[4-[(3,4,5,6-tetrahydro-[1,3,6]triazocino[1,2-a]benzimidazole-1(2H)-yl)sulfonyl]-phenyl]methanesulfonamide, hydrochloride had % $APD_{60}=+28$ and % $V_{max}=-1$. The compound of Example 9, N-[4-[(2,3,5,6-tetrahydro-[1,3,6]triazocino[1,2-a]benzimidazole-4(1H)-yl)sulfonyl]phenyl]methanesulfonamide, hydrochloride, had a % $APD_{60}=+41$ and % $V_{max}=-6$.

In another standard pharmacological procedure to characterize antiarrhythmic activity, anesthetized pigs are pretreated with the test compound (usually i.v. in a dose 1-10 mg/kg), and their ability to survive both acute ligation and reperfusion of the left anterior descending artery is determined. The extent of ectopic activity under these conditions is also determined. In a further standard procedure to characterize antiarrhythmic activity, the ability of the test compound to revert sustained atrial flutter induced by rapid electrical stimulation to pure sinus rhythm is determined. In this procedure laboratory dogs (modified inter-cavo lesion, Rosenbluth-Garcia-Lamos model) are given an i.v. dose of 1-10 mg/kg of the test compound.

Those compounds of the invention which are described above as antiarrhythmic agents are useful in the treatment of cardiac arrhythmias and conditions characterized by coronary artery occlusion and the resulting myocardial ischemia in mammals, particularly in man. For that purpose, such compounds or their non-toxic pharmaceutically acceptable salts, may be administered orally or paranterally in suitable dosage forms compatible with the route of administration, whether oral, intraperitoneal, intramuscular, intravenous, intranasal, buccal, etc. The effective dose range determined in the animal test models has been established at from 1 to about 50 milligrams per kilogram host body weight to be administered in single or plural doses as needed to relieve the arrhythmatic dysfunction. The specific dosage regimen for a given subject will depend upon age, pathological state, severity of dysfunction, size of the subject, etc. Oral administration is performed with either a liquid or solid dosage unit in any conventional form such as tablets, capsules, solutions, etc., which comprise a unit dose (e.g. from about 25 milligrams to about 4 grams) of the active ingredient alone or in combination with adjuvants needed for conventional coating, tableting, solubilizing, flavoring or coloring. Parenteral administration with liquid unit dosage forms may be via sterile solutions or suspensions in aqueous or oleagenous medium. Isotonic aqueous vehicle for injection is preferred with or without stabilizer, preservatives and emulsifiers.

Two alternative routes for the preparation of the novel 1,2,3,4,5,6-hexahydro-[1,3,6]triazocino[1,2-a]-benzimidazole ring system are described below. The invention for which patent protection is sought includes such novel preparative steps and novel intermediate compounds:

Route 1: from 2-aminobenzimidazoles

Generically this reaction sequence can be represented by the following Scheme 1.

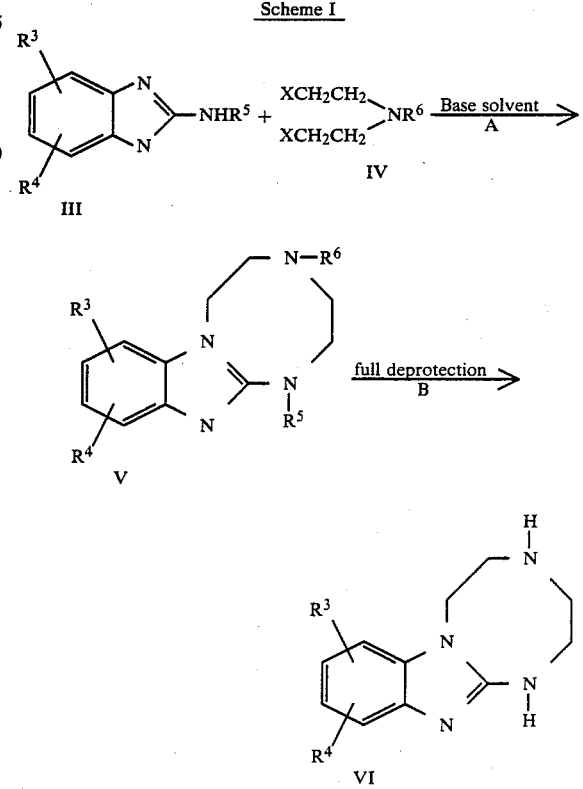

wherein X may be chloro, bromo, or methylsulfonyloxy; $R_5$ may be hydrogen or a removable amino protective group (such as benzoyl, substituted-benzoyl, $C_1$-$C_8$ alkanoyl or cyano), or any other desired value of $R^2$ in Formula II; and $R^6$ may be a removable amino protective group (usually different from that of $R_5$, for example, phenyl) or any other desired value of $R^2$ in Formula I (except hydrogen). X is preferably chloro: $R^5$ is preferably benzoyl, hydrogen or cyano: and $R^6$ is preferably phenyl.

It will be appreciated from the following Scheme 2 that the desired $-SO_2R^1$ moiety may be added to either of the two deprotected 1,2,3,4,5,6-hexahydro-triazocino nitrogens, depending upon the reaction conditions chosen. Or, one of these positions may be left protected or occupied by a nonremovable $R^2$ group and the $-SO_2R^1$ thereby selectively attached to the other position. Such selection is within the skill of the art.

Scheme 1 is illustrated by Examples 1–9 wherein the aforementioned antiarrhythmic agents are obtained in Examples 7, 8 and 9.

In Step A the solvent would preferably be aprotic, such as dimethylsulfoxide, tetrahydrofuran, or N,N- dimethylformamide, the latter of which is preferred. Examples of appropriate bases are sodium hydride, sodium amide, dimsyl sodium, potassium t-butoxide, lithium diisopropylamide and potassium hexamethyldisilazane. 2 moles of base are required, and potassium t-butoxide is the preferred base. Prior to adding reactant IV, for example N,N-bis(chloroethyl)aniline, the reaction mixture is azetropically distilled to remove water. (The reaction of step A is carried out under heating, and under protection from moisture.)

Step B (deprotection) is carried out in a known manner depending upon the nature of the amino-protecting groups $R^5$ and/or $R^6$ or depending upon the desire to have one of $R^5$ or $R^6$ represent $R^2$ in the final product, as described above. The use and removal of protective groups, particularly amino-protective groups, is well known in the peptide and penicillin arts. *Protective Groups In Organic Chemistry,* J. F. W. McOmie, ed., (Plenum Press, London, New York, 1973), among others, describes the use, preparation and selective removal of a large number of protective groups.

In the practice of Route 1 of the invention $R^6$ represented phenyl and $R^5$ represented hydrogen or benzoyl.

Where $R^5$ represented benzoyl and $R^6$ represented phenyl, the benzoyl ($R^5$) group was removed first by treatment with methanolic ammonia at 100° C. The remaining phenyl protective group ($R^6$) was then removed by hydrogenolysis in the presence of dilute hydrochloric acid, dioxane and 10% palladium on carbon [R. Kuhn and H. J. Haas, Ann. 611, 57 (1958)]. The conditions for removal of an $R^5$ benzoyl or like protective group could include treatment with alkali (eg., potassium hydroxide) in hydroxylic solvents (eg. ethanol), alkoxides in alcohols (eg. sodium ethoxide in ethanol with appropriate cosolvents (eg. dioxane or tetrahydrofuran).

Scheme 2 below illustrates the addition of the $R^1SO_2$— moiety to the fully deprotected 1,2,3,4,5,6-hexahydro-[1,3,6]triazocino[1,2-a]benzimidazole ring system (Scheme I, formula VI).

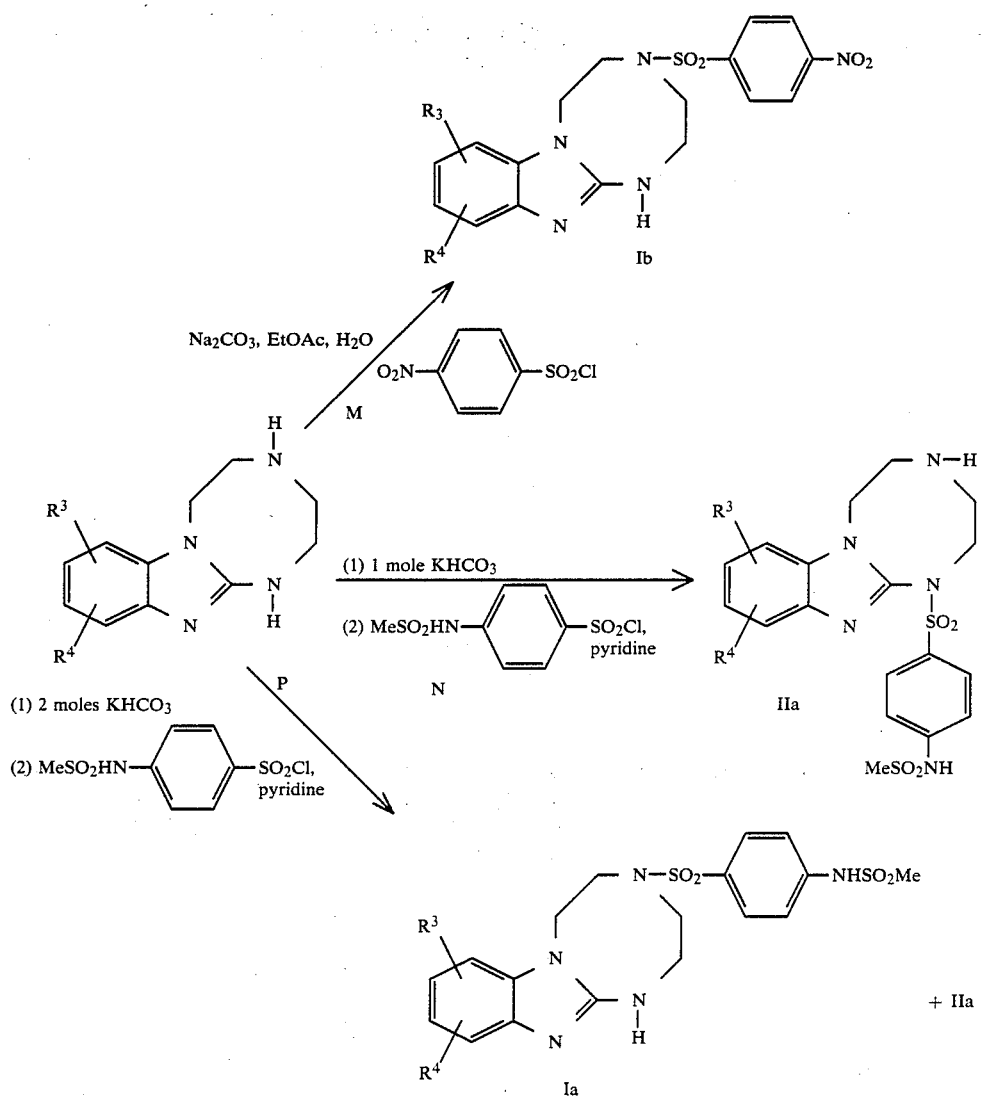

Scheme 2

Step M of Scheme 3 is illustrated in Example 7. Step N is illustrated in Example 8 and Step P is illustrated in Example 9.

Route 2: by conversion of 7-substituted-2,3,4,5-tetrahydro-1H-[1,2,5]triazepino[1,2-a][1,2,4]benzotriazines This novel process to produce the 1,2,3,4,5,6-hexahydro[1,3,6]triazocino[1,2-a][1,2,4]benzotriazines of the invention is illustrated in the following Scheme 3:

appropriate reagent, such as thiourea, followed by methylation. In step C, Cl of formula IV may be replaced by bromine or methylsulfonyloxy (ie. X as defined for formula IV in Scheme 1). Additionally, the benzoyl group in formula VII may be replaced by other suitable amino protective groups, such as a benzyl or a $C_1$–$C_4$ alkanoyl group, Steps C and D of Scheme 2 are

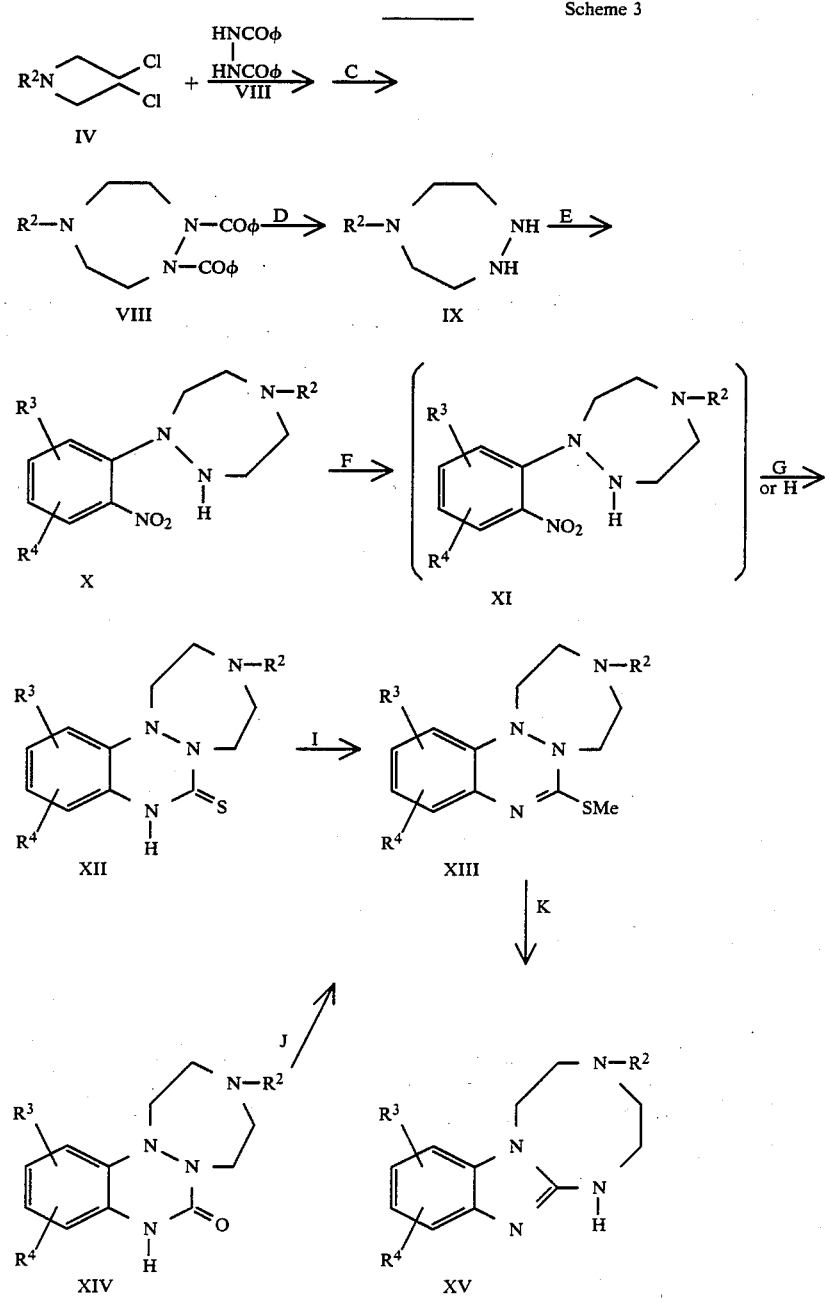

Scheme 3

In Scheme 3, $R^2$, $R^3$ and $R^4$ are as previously defined. The moiety —SMe in formula XIII may be replaced by —Cl or —Br or by =S or =O of formulas XII and XIV, all of which may be represented generically by "Y". =S, =O, and —SMe are preferred Y groups. As shown in step J, Y is =O could be converted to Y is —SMe directly by thiation with $P_2S_5$ followed by methylation or indirectly by chlorination with $POCl_3$ followed by displacement of chlorine by mercapto from an illustrated in Examples 10A and 10B, respectively. Step E is illustrated in Example 10C, and steps F and H are illustrated in Example 11. Steps F and G are illustrated in Examples 12 and 13. Step I, the methylation, is illustrated in Example 14.

Route 2, as shown in Scheme 3, is again illustrated in Examples 15-21 in which $R^2$ represents benzyl (ie. phenylmethyl) rather than phenyl. Step K of Route 2 is variously illustrated in Examples 22, 24 and 25. As illustrated therein, the 2,3,4,5-tetrahydro-7-(methylthio)-1H-[1,2,5]triazepino[1,2-a][1,2,4]benzotriazine ring system (formula XIII, Y is —SMe) is converted to the desired 1,2,3,4,5,6-hexahydro-4-phenyl-[1,3,6]triazocino[1,2-a]benzimidazole ring system (formula XV, $R^2$ is phenyl). In Example 22, N-aminomorpholine was used to effect the ring conversion. In examples 24 and 25, the reducing metal zinc was used to effect the conversion. Other reducing metals, such as aluminum, could be used in place of zinc.

The practice of the invention and the best made therefore is illustrated by the following examples.

Route 1: From 2-Aminobenzimidazoles

EXAMPLE 1

1,2,3,4,5,6-Hexahydro-4-Phenyl[1,3,6]Triazocino[1,2-a]-Benzimidazole (Batch 1)

A mechanically stirred mixture of N-(benzimidazol-2-yl)benzamide (III, $R^5$ is benzoyl) (19.0 g), N,N-dimethylformamide (800 ml) and toluene (100 ml) was azeotropically distilled until 20 ml of distillate had been collected. Potassium t-butoxide (17.5 g) was added and the mixture distilled once more until 80 ml of distillate had been collected. N,N-Bis(chloroethyl)aniline (17.8 g) was added and the mixture was stirred and heated under reflux with protection from moisture for 6 hours. The cooled mixture was filtered and the filtrate was evaporated to a syrup under oil pump vacuum. The syrup was dissolved in warm toluene and the solution was cooled prior to applying it to a column (97×6.3 cm) of dry column grade neutral alumina prepacked in toluene. Elution with toluene removed a faster moving component which was discarded. Fractions were monitored by t.l.c. on Alox-25 $uv_{254}$ plates with chloroform as developer. The column was also monitored visually. Elution with toluene-chloroform (1:1) removed a major slower moving component. Appropriate fractions (ca. 4.1) were evaporated to dryness. The crystalline residue was dissolved in warm chloroform and the solution was decolorized. The solution was concentrated and heptane was added. The resulting crystals (6.78 g, 22%, m.p.=219°-220°) which were crude 1-benzoyl-1,2,3,4,5,6-hexahydro-4-phenyl[1,3,6]triazocino[1,2-a]benzimidazole (7.0 g) and methanol (1200 ml) presaturated with ammonia at 0°, were sealed in a steel bomb and heated in a steam bath for 3 days. The solution was evaporated to dryness. The crystalline residue was extracted with chloroform-toluene (1:1) and the extract applied to a column (51.2×5.2 cm) of dry column grade neutral alumina prepacked in toluene. Elution was with toluene, toluene-chloroform (1:1) and chloroform. Monitoring of fractions was by t.l.c. on Alox-25 $uv_{254}$ plates with chloroform as developer. Fractions containing a major component were evaporated and the residue was crystallized from chloroform-heptane; wt. 3.35 g (66%), mp=154°-156°. Further material (0.5 g) was obtained by processing the mother liquor on a further warm column of alumina. Recrystallization with decolorization with chloroform-heptane gave pure titled product, mp=156°-158°.

Analysis for: $C_{17}H_{18}N_4$; Calculated: C, 73.25; H, 6.52; N, 20.13; Found: C, 72.64; H, 6.32; N, 20.08.

EXAMPLE 2

1-Benzoyl-1,2,3,4,5,6,-Hexahydro-4-Phenyl[1,3,6]-Triazocino[1,2-a]-Benzimidazole A mechanically stirred mixture of N-(1H-benzimidazol-2-yl) benzamide (75.9 g), N,N-dimethylformamide (3.2 l) and toluene (400 ml) was azeotropically distilled until 100 ml of distillate had been collected. Potassium t-butoxide (69.8 g) was added and the mixture was distilled again until a further 300 ml of distillate had been collected. N,N-Bis(chloroethyl)aniline (71.0 g) was added and the mixture was distilled once more until a further 100 ml of distillate had been collected. The mixture was stirred and heated under reflux with protection from moisture for 21 hours. The cooled mixture was filtered through Celite and the filtrate was evaporated under oil pump vacuum. The residual syrup was extracted with dichloromethane. Evaporation of the filtered extract gave a solid. The solid was dissolved in boiling toluene and the solution allowed to cool. The resulting mixture was applied to a column (79×8.4 cm) of dry column grade neutral alumina prepacked in toluene. Elution with toluene removed a fast moving component. Elution with dichloromethane-toluene (1:1) then removed the major component. Appropriate sized fractions (ca 1 l.) were monitored by t.l.c. on Alox-25 $uv_{254}$ plates with chloroform as developer. Evaporation of appropriately pooled fractions, containing the main component, caused crystallization of crude titled product; wt. 31.4 g (26%), mp=217°-220°. T.l.c of this material indicated a small quantity of a lower moving component was contaminating the product. The product was dissolved in dichloromethane (400-500 ml) and toluene added to the cloudy solution. After refrigeration, a small precipitate (0.3 g of the slower component) was removed by filtration. The filtrate was concentrated by boiling until copious crystallization had occurred. After refrigeration crystals of pure titled product were collected on a filter and washed with toluene; wt. 26.9 g (22%), mp=219°-221°.

Analysis for: $C_{24}H_{22}N_4O$; Calculated: C, 75.37; H, 5.80; N, 14.65; Found: C, 75.50; H, 5.74; N, 14.74.

Additional material (2.95 g), (3%), mp=219°-221° was obtained by processing material, crystallized from the mother liquor, as described above.

EXAMPLE 3

1,2,3,4,5,6-Hexahydro-4-Phenyl[1,3,6]Triazocino[1,2-a]Benzimidazole (Batch 2)

A mixture of 1-benzoyl-1,2,3,4,5,6-hexahydro-4-phenyl[1,3,6]triazocino[1,2-a]benzimidazole (10.00 g) from Example 2 and methanolic ammonia (1150 ml), presaturated at 0°, was stirred magnetically and heated in a sealed bomb at 100° for 4 days. The resulting cooled solution was filtered and the filtrate was evaporated to a syrup which crystallized. The residue was dissolved in dichloromethane-methanol and the solution was evaporated to a syrup. Crystallization from methanol gave crude titled product; wt. 5.24 g (72%), mp=158°-159°. The mother liquor was evaporated to a crystalline residue which was subjected to an oil pump vacuum. A solution of the residue in a minimum volume of warm dichloromethane was applied to a column (56×3.2 cm) of dry column grade neutral alumina prepacked in toluene. Elution was with toluene (400 ml), toluene-dichloromethane (4:1, 500 ml) followed by dichloromethane. The product was eluted with dichloromethane. The fractionation was monitored by t.l.c. on Alox-25 uv$_{254}$ plates with dichloromethane-methanol (19:1) as developer. Fractions which contained only product were evaporated to a syrup which crystallized. Recrystallization with decolorization from methanol gave product; wt. 0.93 g (13%), mp=158°-160°. This material, combined with material obtained above, was recrystallized with decolorization from methanol to give pure titled product; wt. 5.46 g, mp=159°-160°.

Analysis for: $C_{17}H_{18}N_4$; Calculated: C, 73.35; H, 6.52; N, 20.13; Found: C, 73.17; H, 6.49; N, 19.91.

EXAMPLE 4

1,2,3,4,5,6-Hexahydro-4-Phenyl[1,3,6]Triazocino[1,2-a]Benzimidazole (Batch 3)

A mechanically stirred mixture of N-(1H-benzimidazole-2-yl)-benzamide (75.9 g), N,N-dimethylformamide (3.2 l) and toluene (400 ml) was azeotropically distilled until 100 ml of distillate had been collected. Potassium t-butoxide (69.8 g) was added and the mixture was distilled again until a further 300 ml of distillate had been collected. N,N-Bis(chloroethyl)-aniline (71.0 g) was added and the mixture was distilled once more until a further 100 ml of distillate had been collected. The mixture was stirred and heated under reflux with protection from moisture for 21 hours. The cooled mixture was filtered and the filtrate was evaporated under oil pump vacuum to a foam. The foam was extracted with dichloromethane and the filtered extract was evaporated to a solid. The solid was extracted with dichloromethane and the filtered extract was evaporated to a brown foam which was subjected to oil pump vacuum; wt. 118.3 g. A portion (107.0 g) of this foam was mixed with methanol (approximately 1 l.) and the mixture was boiled. The hot mixture was filtered and the solid washed with hot methanol. The solid (24.0 g, mp=223°-239°) was discarded. The filtrate was evaporated to a dark red syrup. The syrup was extracted with dichloromethane and the filtered extract was evaporated to a solid, wt. 81.6 g. The solid was dissolved in dichloromethane (500 ml) and evaporated to smaller volume, whereupon crystallizaton of crude 1-benzoyl-1,2,3,4,5,6-hexahydro-4-phenyl[1,3,6]triazocino[1,2-a]benzimidazole occurred. Addition of ether and warming completed crystallization. The crystals were collected on a filter and washed with methanol followed by ether. The crystals were then suspended in ether containing methanol and the mixture stirred magnetically. The resulting white solid was collected on a filter and washed with ether; wt. 23.7 g, (21%), mp=219°-221°.

Analysis for: $C_{24}H_{22}N_4O$; Calculated: C, 75.37; H, 5.80; N, 14.65; Found: C, 74.66; H, 5.89; N, 14.52.

The above material was sufficiently pure (99.2% by HPLC) to be utilized directly in the next step. A mixture of the above material (15.0 g) and methanolic ammonia (1200 ml), presaturated at 0°, was stirred magnetically and heated in a sealed bomb at 100° for 4 days. The resulting cooled solution was filtered and the filtrate was evaporated to a syrup which crystallized. The crystalline residue was dissolved in methanol and the solution was decolorized. The solution was evaporated to smaller volume, warmed and seeded with the titled product. Crystallization was completed by refrigeration. The crystals were collected on a filter and washed in succession with methanol chilled in dry ice-acetone and ether. The slightly colored crystals were promptly recrystallized from methanol as described to give pure titled product; wt. 6.60 g, (60%), mp=159°-161°.

Analysis for: $C_{17}H_{18}N_4$; Calculated: C, 73.35; H, 6.52; N, 20.13; Found: C, 73.13; H, 6.47; N, 19.95.

EXAMPLE 5

1,2,3,4,5,6-Hexahydro-4-Phenyl[1,3,6]Triazocino[1,2-a]Benzimidazole (Batch 4)

A mixture of 2-aminobenzimidazole (III, $R^5$ is hydrogen) (3.00 g), N,N-dimethylformamide (60 ml) and benzene (30 ml) was azeotropically distilled until 15 ml of distillate had been collected. Potassium t-butoxide (2.66 g) was added to this solution and the mixture was azeotropically distilled again until 10 ml of distillate had been collected. A mixture of N,N-bis(2-chloroethyl)aniline (4.76 g), N,N-dimethylformamide (40 ml) and benzene (10 ml) was azeotropically distilled with 10 ml of distillate had been collected. This latter solution was cooled and added dropwise to the stirred prepared solution of 2-aminobenzimidazole at 70° under nitrogen. The mixture was stirred at 70° overnight. The temperature of the mixture was then raised to 120° and potassium t-butoxide (2.66 g) was added. A further portion of potassium t-butoxide (2.66 g) was added after 2 hours. After a further 20 minutes the reaction was allowed to cool. After evaporation of the solvent, the residue was dissolved in ethyl acetate and the solution was washed with water. The solution was dried over sodium sulfate and evaporated to a solid (5.4 g). Upon heating this material with 2-propanol a solid precipitated. The solid (1.88 g) was collected on a filter and the filtrate was evaporated to dryness. The residue was chromatographed on a column (150 g) of silica gel; elution with ethanol-ethyl acetate dichloromethane (3:7:10) yielding a major component in the intermediate fractions. Evaporation of appropriate fractions gave a residue (1.10 g) which was combined with above precipitated solid and recrystallized from ethyl acetate, wt. 1.90 g. Recrystallization from methanol afforded titled product; wt. 1.30 g (21%), mp=158°-160°.

Analysis for: $C_{17}H_{18}N_4$; Calculated: C, 73.35; H, 6.52; N, 20.13; Found: C, 73.43; H, 6.57; N, 20.28.

Route 1: Preparation of Final Products

EXAMPLE 6

1,2,3,4,5,6-Hexahydro-[1,3,6]Triazocino[1,2-a]Benzimidazole, Dihydrochloride, ⅜ Hydrate (Intermediate VI)

A mixture of 1,2,3,4,5,6-hexahydro-4-phenyl[1,3,6]-triazocino[1,2-a]benzimidazole (5.75 g), 0.5 g of 10% palladium on carbon, 75 ml of 1N hydrochloric acid and 250 ml of dioxane was treated with hydrogen gas at ambient temperature and pressure until theoretical uptake was achieved. The mixture was filtered and the filtrate was evaporated to a solid. Recrystallization from methanol afforded pure titled product; wt. 4.20 g (72%), mp=221°-223°.

Analysis for: $C_{11}H_{14}N_4 \cdot 2HCl \cdot \frac{3}{8}H_2O$; Calculated: C, 45.41; H, 6.13; N, 19.26; Cl, 24.37; $H_2O$, 5.40 Found: C, 45.30; H, 6.02; N, 19.01; Cl, 24.76; $H_2O$, 5.26.

EXAMPLE 7

1,2,3,4,5,6-Hexahydro-4-[(4-Nitrophenyl)sulfonyl][1,3,6]Triazocino[1,2-a]Benzimidazole, Hydrochloride (Ib)

To a mixture of 1,2,3,4,5,6-hexahydro-[1,3,6]triazocino[1,2-a]benzimidazole, dihydrochloride, hydrate (2.00 g) sodium carbonate (7.69 g), water (50 ml) and ethyl acetate (100 ml) was added 4-nitrobenzenesulfonyl chloride (1.61 g) in ethyl acetate (25 ml) and the mixture stirred magnetically for 18 hours at room temperature. The yellow solid that precipitated was collected on a filter; wt. 1.55 g, (58%).

A hydrochloride salt of the product was formed in methanol. Recrystallization from 95% ethanol gave pure titled product; wt. 1.40 g, (45%), mp=227 d.

Analysis for: $C_{17}H_{17}N_5SO_4.HCl$; Calculated: C, 48.17; H, 4.28; Cl, 8.37; N, 16.52; S, 7.57; Found: C, 48.45; H, 4.34; Cl, 8.48; N, 16.25; S, 7.54.

EXAMPLE 8

N-[4-[(3,4,5,6-Tetrahydro-[1,3,6]Triazocino[1,2-a]Benzimidazol-1(2H)-yl)Sulfonyl]Phenyl]Methanesulfonamide, Hydrochloride (IIa)

1,2,3,4,5,6-Hexahydro-[1,3,6]triazocino]1,2-a]benzimidazole, dihydrochloride, hydrate (2.05 g) was mixed with water containing potassium bicarbonate (0.70 g) and the mixture evaporated to dryness. The residue was evaporated twice with ethanol and the residue subjected to an oil pump vacuum overnight. The residue was dissolved in dry pyridine (ca. 70 ml) by warming and the solution was evaporated to a solid which was subjected to an oil pump vacuum. The solid was stirred magnetically with pyridine (150 ml, dried over 4A molecular sieves) with protection from moisture, and warmed to achieve solution. The the stirred, cooled solution was added portionwise 4-[(methylsulfonyl)amino]benzenesulfonyl chloride (2.17 g), with protection from moisture. After the reaction mixture had been stirred for three hours at room temperature a precipitate (1.4 g) which had formed was removed by filtration and washed with pyridine and ether. The mother liquor afforded a further 1.6 g of a slightly yellow solid. The mother liquor from this latter material was evaporated to dryness. Each of these three fractions was triturated with water containing potassium bicarbonate. The first crop (1.4 g) yielded 0.54 g of a solid, mp=238°-242°. The second crop yielded 1.10 g of a solid, mp=234°-240°. The final mother liquor yielded 0.66 g of a solid, mp=227°-231°. All of these solids were combined and dissolved in stirred, boiling acetonitrile (800 ml). The solution was filtered through Celite and the filtrate was concentrated by boiling to approximately 250 ml, whereupon crystallization occurred. The solution was allowed to cool and the pure base of the titled product was collected on a filter; wt. 1.88 g (62%), mp=242°-244°.

Analysis for: $C_{18}H_{21}N_5O_4S_2$; Calculated: C, 49,64; H, 4.86; N, 16.08; S, 14.72; Found: C, 50.02; H, 4.79; N, 16.07; S, 15.35.

The above free base (1.80 g) was mixed with methanolic hydrogen chloride (ca. 20 ml). Crystallization was induced by the addition of ether and rubbing. The collected crude titled product [1.85 g (58%), mp=223°-225°] was recrystallized (with decolorization) from methanol-ether; wt.=1.69 g (51%), mp=224°-226°.

Analysis for: $C_{18}H_{21}N_5O_4S_2.HCl$; Calculated: C, 45.81; H, 4.70; Cl, 7.51; N, 14.84; S, 13.59; Found: C, 45.85; H, 4.74; Cl, 7.69; N, 14.49; S, 13.63.

EXAMPLE 9

N-[4-[(2,3,5,6-Tetrahydro-[1,3,6]Triazocino[1,2-a]Benzimidazol-4(1H)-yl)Sulfonyl]Phenyl]Methanesulfonamide (Ia)

A. 1,2,3,4,5,6-Hexahydro-[1,3,6]triazocino[1,2-a]benzimidazole, dihydrochloride, hydrate (2.00 g) was mixed with water containing potassium bicarbonate (1.37 g) and the mixture evaporated to dryness. The residue was coevaporated thrice with ethanol and twice with dry pyridine. The residue was dissolved in pyridine (100 ml, dried over 4A molecular sieves) and the solution stirred magnetically. 4-[(Methylsulfonyl)amino]benzenesulfonyl chloride (2.12 g) was added in portions, with protection from moisture. Stirring was continued until the reagent had dissolved and the mixture was left at room temperature overnight. The reaction mixture was evaporated to a syrup and the syrup was treated with water and potassium bicarbonate. Trituration followed by magnetic stirring gave a solid which was collected on a filter and washed well with water, wt. 2.33 g, mp=225°-243°. This material was the free base of the crude title product contaminated with its isomer, N-[4-[(2,3,5,6-tetrahydro-[1,3,6]triazocino[1,2-a]benzimidazol-1(1H)-yl)sulfonyl]phenyl]methanesulfonamide. The solid was stirred in boiling acetonitrile (500 ml) and the solution filtered through Celite. The colorless filtrate was concentrated by boiling to approximately 240 ml, whereupon crystals formed. The solution was allowed to cool and the almost pure free base of the titled product was collected on a filter; wt. 1.35 g (45%), mp=266°-268°. Further product (0.13 g) was obtained by fractional crystallization of material obtained from the mother liquors. This material was combined with the main crop of crystals and recrystallized from acetonitrile as described; wt. 1.30 g, mp=267°-269°. Approximately 10 ml of warm methanolic hydrogen chloride was added to the crystals and the mixture swirled to achieve solution. Crystals of the titled product started to form. Methanol and ether were added to complete the crystallization. Recrystallization from methanol-ether afforded the titled product as the hydrochloride, 0.4 hydrate; wt. 1.3006 g (40%), mp=202°-203° with prior sintering.

Analysis for: $C_{18}H_{21}N_5O_4S_2.HCl.0.4H_2O$; Calculated: C, 45.11; H, 4.80; Cl, 7.40; N, 14.61; S, 13.38; $H_2O$, 1.50 Found: C, 44.98; H, 5.25; Cl, 7.61; N, 14.60; S, 13.38; $H_2O$, 1.02.

The fractional crystallization described above also gave 0.51 g (17%, mp=242°-244°) of almost pure N-[4-(3,4,5,6-tetrahydro)[1,3,6]triazocino[1,2-a]benzimidazol-1(2H-yl)sulfonyl]phenyl]methanesulfonamide which was similarly converted into its hydrochloride (mp=223°-225°).

B. The titled compound was obtained as the free base in subsequent preparations following similar methodology to that described in this example. It had mp.=266°-267°.

Analysis for: $C_{18}H_{21}N_5O_4S_2$; Calculated: C, 49.64; H, 4.86; N, 16.08; S, 14.72; Found: C, 49.63; H, 4.90; N, 16.19; S, 15.20.

C. N-4-[2,3,5,6-tetrahydro-[1,3,6]triazocino[1,2-a]benzimidazol-4(1H)yl)sulfonyl]phenylmethanesulfonamide (2.413 g) was added to 20 ml of warm methanolic hydrogen chloride and the mixture swirled to achieve solution. Crystals formed and the mixture was allowed to sit at room temperature. Ether was added to complete crystallization. The product was collected on a filter and was washed with ether containing methanol and finally with ether. Drying under vacuum at room temperature gave 2.579 g of material having mp.=196°-203°. That material was recrystallized by boiling down a methanol solution to approximately 20 ml. A few drops of methanolic hydrogen chloride were then added followed by ether. After refrigeration, the resulting crystals were collected on a filter and washed with ether. The crystals were dried at 80° under oil pump vacuum to give 2.4810 g of dehydrated titled product as a hydrochloride salt, which gained water rapidly from the atmosphere. After several hours, the final weight of titled product as the hydrochloride, dihydrate, was 2.6535 g, 94%), mp=192°-200° (sintering from 188°).

Analysis for: $C_{18}H_{21}N_5O_4S_2.HCl.2H_2O$; Calculated: C, 42.56; H, 5.16; Cl, 6.98; N, 13.79; S, 12.62; $H_2O$, 7.09; Found: C, 42.62; H, 4.84; Cl, 6.96; N, 13.72; S, 12.91; $H_2O$, 6.50.

Route 2: By conversion of 7-substituted-2,3,4,5-tetrahydro-1H[1,2,5]triazepino[1,2-a][1,2,4]benzotriazines

EXAMPLE 10

Hexahydro-1-(2-Nitrophenyl)-5-Phenyl-1H-1,2,5-Triazepine (Xa)

A. 1,2-dibenzoylhexahydro-5-phenyl-1H-1,2,5-triazepine (VIIIa)

A mixture of N,N-dibenzoylhydrazine (VII) (140 g) in N,N-dimethylformamide (6 l) and benzene (500 ml) was azeotropically dried by the distillation of 700 ml of solvent. Potassium t-butoxide (130.4 g) and benzene (500 ml) were then added and the mechanically stirred mixture was distilled once more to remove 700 ml of solvent. Bis(chloroethyl)aniline (IV, $R^2$ is phenyl) (126.9 g) was added and the transfer was completed by the addition of a small volume of dry (4A molecular sieves) N,N-dimethylformamide. The mixture was stirred and heated under reflux with protection from moisture for 5½ hours. The cooled mixture was filtered through celite and the filtrate was evaporated to a solid under oil pump vacuum. The solid was mixed with ether, collected on a filter and air dried. The solid was extracted with boiling benzene (3 l) and the extract was filtered through Celite to remove unreacted N,N'-dibenzoylhydrazine. The filtrate was warmed on a steam bath and left to cool to room temperature overnight. A further small quantity of N,N'-dibenzoylhydrazine was removed by filtration through Celite and the resulting solution was evaporated to small volume (under 1 l). Warming caused crystallization. Addition of ether completed crystallization of the titled compound; wt. 96.0 g (42.7%), mp=190°-192°.

Analysis for: $C_{24}H_{23}N_3O_2$; Calculated: C, 74.78; H, 6.01; N, 10.90; Found: C, 75.20; H, 5.82; N, 10.72.

B. hexahydro-5-phenyl-1H-1,2,5-triazepine dihydrochloride

A mixture of 1,2-dibenzoylhexahydro-5-phenyl-1H-1,2,5-triazepine (101.3 g), n-butanol (450 ml), 12N hydrochloric acid (915 ml) and water (915 ml) was mechanically stirred and heated under reflux on a steam bath overnight. Additional 12N hydrochloric acid (400 ml) and water (400 ml) were added and stirring and heating under reflux on a steam bath were continued for three days. n-Butanol (150 ml) was added and stirring and heating under reflux on a steam bath were continued for a further three days. After this time (7 days) the solid had dissolved. The mixture was extracted twice with ether and the aqueous solution was evaporated to smaller volume. Coevaporation with ethanol and concentrated hydrochloric acid caused crystallization of the titled product; wt. 57.5 g (66%), mp=211°-218°.

Analysis for: $C_{10}H_{15}N_3.2HCl$; Calculated: C, 48.01; H, 6.85; N, 16.80; Cl, 28.34; Found: C, 47.84; H, 7.01; N, 16.62; Cl, 28.04.

C. hexahydro-1-(2-nitrophenyl)-5-phenyl-1H-1,2,5-triazepine

A mixture of hexahydro-5-phenyl-1H-1,2,5-triazepine dihydrochloride (15.0 g), 1-fluoro-2-nitrobenzene (9.84 ml), N,N-diisopropylethylamine (36.5 ml) in N,N-dimethylformamide (150 ml) was magnetically stirred and heated at 75°-80° for 5 hours under nitrogen. The solution was evaporated under oil pump vacuum and the residual syrup was mixed with chloroform and dilute sodium hydroxide. The aqueous phase was extracted once more with chloroform and the combined chloroform extracts were dried ($MgSO_4$). The solution was evaporated to a syrup which was subjected to an oil pump vacuum. This material in benzene was applied to a column (80×4.0 cm) of dry column grade neutral alumina (Woelm) prepacked in benzene. Elution was with benzene and monitoring of fractions was by t.l.c. on Alox 25 $uv_{254}$ plates (Brinkmann) with benzene as developer. The fractions containing the major component were evaporated to a syrup which was crystallized from benzeneheptane; wt. 13.82 g (78%), mp=118°-120°. Recrystallization from benzeneheptane gave pure titled product, mp=119°-121°.

Analysis for: $C_{16}H_{18}N_4O_2$; Calculated: C, 64.41; H, 6.08; N, 18.78; Found: C, 64.76; H, 6.17; N, 18.82.

EXAMPLE 11

2,3,4,5-Tetrahydro-3-Phenyl-1H-[1,2,5]Triazapino[1,2-a][1,2,4]Benzotriazine-7(8H)-One (XIV)

Hexahydro-1-(2-nitrophenyl)-5-phenyl-1H-1,2,5-triazepine (10.0 g) in 1,2-dimethoxyethane (500 ml) was hydrogenated over 10% palladium on carbon (2 g) at atmospheric pressure and room temperature until theoretical uptake was achieved. The mixture was filtered through Celite and the filter pad was washed with 1,2-dimethoxyethane. The filtrate was evaporated to approximately 100 ml and 1,1'-carbonyl-dimidazole (11 g) was added. The mixture, protected from moisture, was swirled and heated under reflux on a steam bath for 4 hours. The solution was evaporated to dryness. The residue in chloroform was applied to a column (75×5.4 cm) of dry column grade neutral alumina prepacked in chloroform. Elution was with chloroform and monitoring of fractions was by t.l.c. on Alox-25 $uv_{254}$ plates (Brinkmann) with chloroform-methanol (9:1) as developer. The fractions containing the major component were evaporated to dryness and the residue was crystallized from chloroform-ether; wt. 7.45 g (75%), mp=196°-198°. Three crystallizations from the same solvent system gave titled product, mp=198°-199°.

Analysis for: $C_{17}H_{18}N_4O$; Calculated: C, 69.37; H, 6.16; N, 19.04; Found: C, 68.80; H, 6.25; N, 18.70.

EXAMPLE 12

2,3,4,5-Tetrahydro-3-Phenyl-1H-[1,2,5]Triazepino[1,2-a][1,2,4]Benzotriazine-7(8H)-Thione (XIIa) (Batch 1)

Hexahydro-1-(2-nitrophenyl)-5-phenyl-1H-1,2,5-triazepine (22.4 g) was hydrogenated in 1,2-dimethoxyethane (800 ml) as in Example 11 and the volume reduced to 250 ml. 1,1'-Thiocarbonyldiimidazole (27 g) was added and the mixture, protected from moisture, was heated under reflux on a steam bath overnight. The solution was evaporated to dryness. The residue was dissolved in toluene and applied to a column (63×8.0 cm) of dry column grade neutral alumina prepacked in toluene. Elution with toluene (several liters) removed a faster moving yellow component from the column. The eluting solvent was changed to toluene-chloroform (4:1, 2 l) and then to chloroform. Monitoring of fractions was by t.l.c. on Alox-25 $uv_{254}$ plates (Brinkmann) with chloroform as developer and on silica gel GF (Analtech) plates with chloroform as developer. A slightly faster moving minor purple component was eluted in the earlier fractions containing the major component. In later fractions a slower moving yellow component contaminated the major component. The first fraction (having none of the slower yellow minor component) were evaporated to smaller volume. Coevaporation with toluene caused crystallization. Addition of heptane completed the process; wt. 12.46 g (crop 1), mp=206°–208°. The later yellow fractions similarly gave 5.33 g (crop 2), mp=203°–208° of crude titled product. Recrystallization of crop 2 (from chloroform-toluene-heptane) gave material which was combined with crop 1. This material was dissolved in chloroform and the solution was decolorized. Evaporation to smaller volume followed by coevaporation with toluene and addition of heptane gave 17.6 g (76%) of crude titled product, mp=205°–209°. Recrystallization from the same solvent system gave titled product, mp=205°–208°.

Analysis for: $C_{17}H_{18}N_4S$; Calculated: C, 65.78; H, 5.84; N, 18.05; S, 10.33; Found: C, 62.25; H, 6.00; N, 17.74; S, 9.92

This material was used in Example 14.

EXAMPLE 13

2,3,4,5-Tetrahydro-3-Phenyl-1H-[1,2,5]Triazepino[1,2-a][1,2,4]Benzotriazine-7(8H)-Thione (XIIa) (Batch 2)

Hexahydro-1-(2-nitrophenyl)-5-phenyl-1H-1,2,5-triazepine (5.0 g) was hydrogenated in 1,2-dimethoxyethane (300 ml) as in Example 11 and the resulting solution divided into two equal aliquots. One aliquot was concentrated to approximately 50 ml and 1,1'-thiocarbonyldiimidazole (3.0 g) was added. The solution was protected from moisture and was heated under reflux overnight. Evaporation gave a syrup which crystallized. This material in benzene was applied to a column (45×3.2 cm) of cry column grade neutral alumina prepacked in benzene. Elution with benzene removed a minor yellow component from the column. Elution with chloroform removed the major component contaminated with a minor faster moving purple component and a minor slower moving, yellow component. Monitoring of fractions was by t.l.c. on Alox-25 $uv_{254}$ plates (Brinkmann) with ethyl acetate-methanol (19:1) as developer. Evaporation of appropriate fractions gave a residue which crystallized from benzene; wt. 1.49 g (57%), mp=202°–206°. Recrystallization from benzene gave titled product, mp=206°–208°.

Analysis for: $C_{17}H_{18}N_5S$; Calculated: C, 65.78; H, 5.84; N, 18.05; S, 10.33; Found: C, 65.85; H, 5.84; N, 18.04; S, 10.44.

EXAMPLE 14

2,3,4,5-Tetrahydro-7-(Methylthio)-3-Phenyl-1H-[1,2,5]Triazepino[1,2-a][1,2,4]Benzotriazine (XIIIa)

To a mixture of 2,3,4,5-tetrahydro-3-phenyl-1H-[1,2,5]triazepino[1,2-a][1,2,4]benzotriazine-7(8H)-thione (3.1 g from Example 12) and potassium t-butoxide (1.29 g) in N,N-dimethylformamide (50 ml, dried over 4A molecular sieves) was added methyl iodide (2 ml) and the reaction flask was sealed rapidly. An exothermic reaction ensued. The solution was left at room temperature overnight. The solution was evaporated and the residue was extracted with chloroform. The extract was applied to a column (71×3.2 cm) of dry column grade neutral alumina prepacked in chloroform. Elution with chloroform furnished a major component. Appropriate fractions were evaporated to a syrup. Trituration with heptane gave crude titled product; wt. 2.21 g, (65%), mp=125°–127°. Recrystallization (with decolorization) from dichloromethane-heptane furnished pure product; mp=128°–130°, m/e (E.I.) 324; $_{max}^{KBr}$ 1589, 765, 748, 693 cm$^{-1}$; pmr (100 MHz, DMSO-D$_6$) 2.42 (3H, singlet), 3.29 (2H, triplet, J=6 Hz), 3.67 (2H, triplet, J=6 Hz), 3.81 (2H, triplet, J=6 Hz), 3.89 (2H, triplet, J=6 Hz), 6.64–7.34 (9H, overlapping multiplets).

Analysis for: $C_{18}H_{20}N_4S$; Calculated: C, 66.64; H, 6.21; N, 17.27; S, 9.88; Found: C, 66.24; H, 6.27; N, 17.19; S, 10.27.

EXAMPLE 15

1,2-Dibenzoylhexahydro-5-(Phenylmethyl)-1H-1,2,5-Triazepine (VIIIb)

A mixture of N,N'-dibenzoylhydrazine (8.61 g) and potassium t-butoxide (13.7 g) in N,N-dimethylformamide (500 ml) and benzene (100 ml) was azeotropically distilled until 110 ml of distillate had been collected. N-Benzyl-N,N-bis(chloroethyl)amine hydrochloride (10.7 g) was added and rinsed into the reaction with 50 ml of N,N-dimethylformamide (dried over 4A molecular sieves). The mixture was stirred and heated under reflux for 5 hours. The mixture was filtered through Celite and the filter pad was washed with N,N-dimethylformamide. The filtrate and washings were evaporated under oil pump vacuum to a syrup. The syrup in benzene was applied to a column (54×4.0 cm) of dry column grade neutral alumina prepacked in benzene. Elution was with benzene, benzene-chloroform (9:1) and benzene-chloroform (4:1). The product was eluted with the chloroform containing solvents. Fractions were monitored by t.l.c. on Alox-25 $uv_{254}$ plates (Brinkmann) with chloroform-ethyl acetate (7:3) as developer. (A marker of 1,2-dibenzoylhexahydro-5-phenyl-1H-1,2,5-triazepine, which ran with a similar Rf to the titled product, was useful in detecting the product in this fractionation). Appropriate fractions were evaporated to a syrup which was crystallized from benzene-heptane; wt. 4.68 g (29%), mp=135°–138°. Recrystallization (with decolorization) from the same solvents gave the titled product, mp=141°–143°.

Analysis for: $C_{25}H_{25}N_3O_2$; Calculated: C, 75.16; H, 6.31; N, 10.52; Found: C, 75.18; H, 6.21; N, 10.49.

Route 2: Preparation of Intermediate XVI from Hexahydro-5-(Phenylmethyl)-1H-1,2,5-Triazepine Starting Material

EXAMPLE 16

Hexahydro-1-5-(Phenylmethyl)-1H-1,2,5-Triazepine (IXb)

A mixture of 1,2-dibenzoylhexahydro-5-(phenylmethyl)-1H-1,2,5-triazepine (15.0 g), n-butanol (250 ml), concentrated hydrochloric acid (250 ml) and water (250 ml) was stirred and treated under reflux for 3 hours. The mixture was diluted with water and ether. The aqueous layer was separated and washed with ether ($\times 4$) and evaporated to smaller volume. A small quantity (0.2 g) of starting material, deposited at this stage, was removed by filtration. Further evaporation and addition of 2-propanol (and seeds) caused crystallization of crude titled product; wt. 8.32 g (84%), mp=166°–169°. This material was dissolved in methanol containing concentrated hydrochloric acid. The solution was decolorized and evaporated to smaller volume. Addition of 2-propanol and warming gave the titled product, mp=171°–173°.

Analysis for: $C_{11}H_{17}N_3.2HCl$; Calculated: C, 50.01; H, 7.25; Cl, 26.84; N, 15.90; Found: C, 49.59; H, 7.16; Cl, 26.95; N, 15.91.

EXAMPLE 17

Hexahydro-1-(2-Nitrophenyl)-5-(Phenylmethyl)-1H-1,2,5-Triazepine (Xb)

A mixture of hexahydro-5-(phenylmethyl)-1H-1,2,5-triazepine dihydrochloride (35.0 g), 1-fluoro-2-nitrobenzene (21 ml), N,N-diisopropylethylamine (81 ml) in N,N-dimethylformamide (400 ml) was stirred and heated at 75°–80° (under reflux) under nitrogen for 5 hours. The solution was evaporated to a syrup under oil pump vacuum and the residue was mixed with chloroform and dilute sodium hydroxide. The aqueous phase was extracted several times with chloroform. The combined extracts were dried ($MgSO_4$) and evaporated to a syrup wich was subjected to an oil pump vacuum. The syrup in toluene was applied to a column ($94 \times 8.7$ cm) of dry column grade neutral alumina prepacked in toluene. Elution with toluene removed a faster moving yellow impurity. Fractions were monitored by t.l.c. on Alox-25 $uv_{254}$ plates (Brinkmann) with chloroform as developer. As soon as the major component started to issue the eluting solvent was changed to toluene-chloroform (4:1), toluene-chloroform (1:1) and finally chloroform. Appropriate fractions were evaporated to a syrup which was crystallized from ether-heptane; wt. 35.7 g (86%), mp=90°–92°. Recrystallization from chloroform-ether-heptane gave pure titled product, mp=90°–92°.

Analysis for: $C_{17}H_{20}N_4O_2$; Calculated: C, 65.36; H, 6.45; N, 17.94; Found: C, 65.35; H, 6.60; N, 18.01.

EXAMPLE 18

2,3,4,5-Tetrahydro-3-(Phenylmethyl)-1H[1,2,5]Triazepino[1,2-a][1,2,4]Benzotriazine-7(8H)-One (XIVb)

Hexahydro-1-(2-nitrophenyl)-5-(phenylmethyl)-1H-1,2,5-triazepine (10.0 g) in 1,2-dimethoxyethane (250 ml) was hydrogenated at over 10% palladium on carbon (2.5 g) at room temperature and atmospheric pressure until theoretical uptake had been achieved. At this stage the reaction solution was colorless and t.l.c. on Alox-25 $uv_{254}$ plates (Brinkmann) with ethyl acetate as developer showed a single component. The mixture was filtered through Celite and the filter pad washed with 1,2-dimethyloxyethane. The filtrate was evaporated to approximately 150 ml and 1,1-carbonyldiimidazole (20 g) was added. The solution was evaporated to dryness and the residue was dissolved in chloroform and applied to a column ($75 \times 6.4$ cm) of dry column grade neutral alumina prepacked in chloroform. Elution with chloroform removed a major component from the column. Fractions were monitored by t.l.c. on Alox-25 $un_{254}$ plates with ethyl acetate as developer. Appropriate fractions were evaporated and the crude titled product was crystallized from chloroform-heptane (seeding); wt. 7.56 g (77%), mp=129°–131°. Two crystallizations from the same solvent gave pure product, mp=127°–128°.

Analysis for: $C_{18}H_{20}N_4O$; Calculated: C, 70.11; H, 6.54; N, 18.17; Found: C, 69.88; H, 6.45; N, 18.01.

EXAMPLE 19

2,3,4,5-Tetrahydro-3-(Phenylmethyl)-1H-[1,2,5]Triazepino[1,2-a][1,2,4]-Benzotriazine-7(8H)-Thione (XIIb)

Hexahydro-1-(2-nitrophenyl)-5-(phenylmethyl)-1H-1,2,5-triazepine (10.0 g) was hydrogenated in 1,2-dimethoxyethane (250 ml) as in example 11 and the volume reduced to approximately 150 ml. 1,1'-Thiocarbonyldiimidazole (20 g) was added and the solution refluxed with protection from moisture overnight. The solution was evaporated to dryness and the residue, dissolved in chloroform, was applied to a column ($72 \times 6.3$ cm) of dry column grade neutral alumina prepacked in chloroform. Elution with chloroform provided a major component. Evaporation of appropriate fractions gave a product which was difficult to crystallize. This material was subjected to further fractionation on a column ($67.5 \times 4.2$ cm) of the same absorbent with chloroform as eluting solvent. Fractions were monitored by t.l.c. on Alox-25 $uv_{254}$ plates with ethyl acetate as developer. Evaporation of homogenous fractions provided material which was crystallized from chloroform-heptane; wt. 5.35 (51%), mp=124°–126°. Recrystallization (with decolorization) from the same solvents gave pure titled product, mp=125°–127°.

Analysis for: $C_{18}H_{20}N_4S$; Calculated: C, 66.64; H, 6.21; N, 17.27; S, 9.88; Found: C, 66.42; H, 6.28; N, 17.17; S, 9.89.

EXAMPLE 20

2,3,4,5-Tetrahydro-1H-[1,2,5]Triazepin[1,2-a][1,2,4]Benzotriazin-7-(8H)-One, Hydrochloride (XIVc)

2,3,4,5-Tetrahydro-3-(phenylmethyl)-1H-[1,2,5]triazepinol[1,2-a][1,2,4]benzotriazine-7(8H)-one (4.58 g) (Example 18) in anhydrous methanol (150 ml) containing glacial acetic acid (4.6 ml) was hydrogenated over 10% palladium on carbon (0.80 g) at room temperature and atmospheric pressure until theoretical uptake had been achieved. The mixture was filtered through Celite and the filter pad washed with methanol. The filtrate and washings were evaporated to a syrup which was dissolved in 2-propanol containing hydrogen chloride. Addition of ether and seeds caused crystallization of crude titled product. Recrystallization with decolorization from methanol-ether gave pure product, wt. 3.28 g (83%), mp=287°–289°.

Analysis for: $C_{11}H_{14}N_4O\cdot HCl$; Calculated: C, 51.87; H, 5.94; Cl, 13.92; N, 22.00; Found: C, 51.65; H, 5.85; Cl, 13.71; N, 22.01.

EXAMPLE 21

2,3,4,5-Tetrahydro-1H-[1,2,5]triazepino[1,2-a][1,2,4]benzotriazepin 7-(8H)-One, Hydrochloride (XIVc)

A mixture of 2,3,4,5-Tetrahydro-3-phenyl-1H-[1,2,5]triazepino[1,2-a][1,2,4]benzotriazine-7(8H)-one (0.294 g), methanol (20 ml), N-hydrochloric acid (3 ml), 10% palladium on carbon (0.1 g) was hydrogenated for several hours at room temperature and atmospheric pressure until theoretical uptake had been achieved and the solid had dissolved. The mixture was filtered through Celite and the filtrate was evaporated to a solid. Recrystallization from methanol-ether afforded titled product, wt. 0.192 (76%), mp=286°–288°. The i.r. and pmr spectra of this material were identical to those obtained in example 20.

Analysis for: $C_{11}H_{14}N_4O\cdot HCl$; Calculated: C, 51.87; H, 5.94; Cl, 13.91; N, 22.00; Found: C, 51.79; H, 6.17; Cl, 13.70; N, 21.95.

EXAMPLE 22

1,2,3,4,5,6-Hexahydro-4-Phenyl-[1,3,6]Triazocino[1,2-a]Benzimidazole (XVa)

2,3,4,5-Tetrahydro-7-(methylthio)-3-phenyl-1H-[1,2,5]triazepino[1,2-a][1,2,4]benzotriazine (3.00 g) (prepared as in Example 14) in N-aminomorpholine (50 ml) under nitrogen was stirred and heated under reflux for 40 hours. The solution was evaporated under oil pump vacuum to a dry syrup, which was coevaporated with toluene to dryness. A solution of this material in toluene was applied to a column (51×2.4 cm) of dry column grade neutral alumina prepacked in toluene. Elution was with toluene (1100 ml), toluene-chloroform (4:1, 1000 ml) and toluene-chloroform (1:1 approximately 2 l.). Fractions of 100 ml or 50 ml were collected where appropriate and these were monitored by t.l.c. on Alox-25 uv$_{254}$ plates with chloroform as developer. The first component, eluted with toluene, was starting material, Rf 0.92. Elution with toluene-chloroform (1:1) initially removed fractions containing two mixed components (Rfs 0.68 and 0.43) and later fractions containing only the major component with Rf 0.34. Fractions containing the major component were evaporated to small volume whereupon crystallization occurred. Heptane was added and the crystals of crude titled product were collected on a filter; wt. 1.06 g (41%), mp=140°–143°. Two recrystallizations from chloroform-heptane with decolorization gave pure product, mp=155°–157°, m/e (E.I.) 278; pmr (300 MHz, 10 mg/ml, CDCl$_3$) 3.60 (2H, triplet, J=6 Hz), 3.70 (2H, triplet, J=6 Hz), 3.74 (2H, triplet, J=6 Hz), 4.46 (2H, triplet, J=6 Hz), 5.03 (1H, broad exchangeable singlet), 6.70 (2H, doublet, J=9 Hz), 6.76 (1H, triplet, J=9 Hz), 7.14–7.34 (5H, overlapping multiplets), 7.52–7.60 (1H, multiplet). The pmr spectrum was shown to be strongly dependant on concentration.

This compound was found to exhibit polymorphism. Crystals could be obtained from chloroform-heptane having mps as low as 143°–144° and as high as 156°–157°. Recrystallization from methanol, however, of the above material (mp. 155°–157°) gave product having: mp=159°–160°; MH+ (C.I.) 279; $\nu_{max}^{KBr}$ 3190, 1613, 1590, 1565, 742, 728, 684 cm$^{-1}$. No polymorphism was observed when this solvent was used for crystallization.

Analysis for: $C_{17}H_{18}N_4$; Calculated: C, 73.35; H, 6.52; N, 20.13; Found: C, 72.75; H, 6.41; N, 20.11.

EXAMPLE 23

2,3,4,5-Tetrahydro-N-(4-morpholinyl)-3-phenyl-1H-[1,2,5]triazepino[1,2-a][1,2,4]benzotriazine-7-amine Fractions containing the two mixed components (Rfs 0.68 and 0.43) obtained from the chromatographic fractionation in Example 22 were evaporated to a syrup. The component with Rf 0.68 was 2,3,4,5-tetrahydro-3-phenyl-1H-[1,2,5]triazepino[1,2-a]-[1,2,4]benzotriazine-7(8H)thione and the component with Rf 0.43 was the titled compound. The two compounds were separated by fractional crystallization from chloroform-heptane. The thione, the origin of which remains unknown, was the more insoluble material; wt. 0.12 g (4%), mp=211°–212°.

Analysis for: $C_{17}H_{18}N_4S$; Calculated: C, 65.78; H, 5.84; N, 18.05; Found: C, 65.63; H, 6.11; N, 18.06.

The titled product (0.41 g, 12%) had mp=142°–144°.

Analysis for: $C_{21}H_{26}N_6O$; Calculated: C, 66.64; H, 6.92; N, 22.21; Found: C, 66.35; H, 7.14; N, 22.05.

EXAMPLE 24

1,2,3,4,5,6-Hexahydro-4-phenyl-[1,3,6]triazocino[1,2-a]benzimidazole

A mixture of 2,3,4,5-tetrahydro-7-(methylthio)-3-phenyl-1H-[1,2,5]-triazepino[1,2-a][1,2,4]benzotriazine (0.5000 g), zinc dust (2.0 g), N,N-dimethylformamide (16 ml) and water (4 ml) was stirred magnetically and heated under reflux for 20 hours. The cooled mixture was filtered through Celite and the filter pad washed with N,N-dimethylformamide. The filtrate and washings were evaporated under oil pump vacuum to a syrup. The syrup was dissolved in dichloromethane and applied to the edges of 4 plates of Alox-100 uv$_{254}$ (20×20 cm×1 mm). The plates were developed twice in dichloromethane and several times in chloroform. The major band was excised and the component eluted by stirring with methanol. The adsorbent was filtered and washed with methanol. The filtrate and washings were evaporated to a syrup. The syrup was extracted with dichloromethane and the solution was evaporated to a syrup which crystallized. The crystals were dissolved in dichloromethane and the solution was treated with charcoal and filtered through Celite. Evaporation gave a syrup which was crystallized from dichloromethane-heptane; wt. 0.127 g (30%), mp=155°–157°.

Analysis for: $C_{17}H_{18}N_4$; Calculated: C, 73.35; H, 6.52; N, 20.13; Found: C, 73.31; H, 6.56; N, 19.60.

EXAMPLE 25

1,2,3,4,5,6-Hexahydro-4-phenyl-[1,3,6]triazocino[1,2-a]benzimidazole

A mixture of 2,3,4,5-tetrahydro-7-(methylthio)-3-phenyl-1H[1,2,5]triazepine[1,2-a][1,2,4]benzotriazine (2.00 g), zinc dust (8.0 g), N,N-dimethylformamide (64 ml) and water (16 ml) was stirred magnetically and heated under reflux for 20 hours. The mixture was filtered through Celite and the filter pad was washed with N,N-dimethylformamide. The filtrate and washings were evaporated under oil pump vacuum to a syrup. The syrup was dissolved in dichloromethane and applied to a column (30×3.0 cm) of dry column grade neutral alumina prepacked in toluene. The mixture was washed with toluene. Elution was with toluene-dichloromethane (4:1) followed by toluene-dichloromethane (1:1), dichloromethane, and finally dichloromethane-methanol (19:1). Fractions containing the major component, as determined by t.l.c. on Alox-25 uv$_{254}$ plates with dichloromethane-methanol (19:1) as developer were evaporated to a foam (1.19 g). T.l.c. indicated that this material was still contaminated with mainly slower moving components. Preparative thin layer chromatography on 8 plates of Alox-25 uv$_{254}$ (20×20 cm×0.25 mm) with chloroform as developer gave a separation of the components. The major middle band was excised and the component eluted by stirring with methanol. The adsorbent was filtered and washed with methanol. The filtrate and washings were evaporated to a solid. The solid was extracted with dichloromethane and the solution evaporated to a foam. The foam was dissolved in dichloromethane and the cloudy solution filtered through Celite. The filtrate was evaporated to a syrup which was crystallized from methanol; wt. 0.35 g, (20.45%), mp=158°–160°. Additional material [0.16 g (9.36%), mp=158°–160°] was obtained from the mother liquors by further preparative thin layer chromatography as described. Recrystallization of both crops from methanol gave 0.38 g of titled product having mp=159°–160°.

Analysis for: $C_{17}H_{18}N_4$; Calculated: C, 73.35; H, 6.52; N, 20.13; Found: C, 73.66; H, 6.65; N, 20.00.

What is claimed is:

1. A compound of the formula

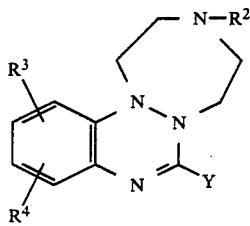  XIII

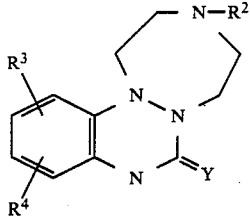  XII wherein

Y of formula XIII is —SMe, —Cl or —Br and Y of formula XII is =S or =O;

$R^2$ may be hydrogen, $C_1$–$C_8$ alkyl, phenyl($C_1$–$C_4$)alkyl or substituted-phenyl($C_1$–$C_4$)alkyl in which phenyl may have one to three substituents selected from $C_1$–$C_4$ alkyl, $C_1$–$C_4$ alkoxy, fluorine, chlorine or bromine, phenyl or substituted-phenyl in which the phenyl substituents are the same as for substituted-phenyl($C_1$–$C_4$)alkyl, 2- or 4-pyrimidinyl, pyrazinyl, imidazolyl, $C_1$–$C_4$ alkanoyl, halo or dihalo-($C_1$–$C_4$)alkanoyl, in which halo is fluoro or chloro, benzoyl or benzoyl substituted on the phenyl ring by one or two $C_1$–$C_4$ alkyl groups, $C_1$–$C_4$ alkanoyloxy, $C_1$–$C_4$ alkylamino($C_1$–$C_4$)alkanoyl, $C_1$–$C_4$ alkyloxycarbonyl, $C_1$–$C_4$ alkylaminocarbonyl, phenylaminocarbonyl in which phenyl may have one to three $C_1$–$C_4$ alkyl groups, phenyloxy or naphthyloxy($C_1$–$C_4$)alkyl in which the phenyl or naphthyl ring may be substituted by one to three $C_1$–$C_4$ alkyl groups, $C_1$–$C_4$ alkylsulfonyl, N-($C_1$–$C_4$)-alkyl- or N-di-($C_1$–$C_4$alkyl)carboxamido-($C_1$–$C_4$)alkyl, N-phenyl or substituted phenylcarboxamido($C_1$–$C_4$)alkyl in which phenyl may be substituted as above for $C_1$–$C_4$alkyl-substituted phenyl, cyano, amidino in which each N atom is substituted by a $C_1$–$C_4$ alkyl group, and $C_1$–$C_4$ alkylguanidino, and $R^3$ and $R^4$ are, independently, hydrogen, $C_1$–$C_4$ alkyl, $C_1$–$C_4$ alkoxy, fluorine and chlorine, or acid addition salts thereof.

2. A compound of claim 1 in which Y is —SMe, =S or =O.

3. A compound of claim 1 in which $R^2$ is $C_1$–$C_8$ alkyl, $C_1$–$C_4$ alkylphenyl, 2 or 4-pyrimidinyl, pyrazinyl, imidazolyl, halo or dihalo-($C_1$–$C_4$)alkanoyl, substituted benzoyl, $C_1$–$C_4$ alkylamino($C_1$–$C_4$)alkanoyl, phenyloxy or naphthyloxy($C_1$–$C_4$)alkyl, $C_1$–$C_4$ alkylsulfonyl, N-($C_1$–$C_4$)alkyl or N-di-($C_1$–$C_4$alkyl)-carboxamido($C_1$–$C_4$)alkyl, or $C_1$–$C_4$ alkylguanidino.

4. A compound of claim 1 in which $R^2$ is $C_1$–$C_6$ alkyl, $C_1$–$C_4$ alkylphenyl, $C_1$–$C_4$ alkyl-substituted-phenyl in which phenyl may have one or two $C_1$–$C_4$ alkyl or chloro substituents, 4-pyrimidinyl, $C_1$–$C_4$ alkylamino($C_1$–$C_4$)alkanoyl, ($C_1$–$C_4$ alkyl)benzyl, N-di-($C_1$–$C_4$alkyl)carboxamido($C_1$–$C_4$)alkyl, N-phenyl or substituted-phenylcarboxamido($C_1$–$C_4$)alkyl, or $C_1$–$C_4$ alkylguandino.

5. A compound of claim 1 in which $R^2$ is $C_1$–$C_4$ alkyl, benzyl, phenyl, 4-pyrimidinyl, (N-dimethyl or diethyl)-carboxamidomethyl or ethyl, N-(2,6-dichlorophenyl)aminocarbonyl, or ethylguanidino.

6. A compound of claim 1 in which $R^3$ and $R^4$ are, independently, hydrogen, methyl or ethyl.

7. A compound of claim 1 in which $R^3$ and $R^4$ are hydrogen.

8. A compound of claim 1 which is 2,3,4,5-tetrahydro-3-phenyl-1H-[1,2,5]triazepino[1,2-a][1,2,4]benzotriazin-7(8H)-one.

9. A compound of claim 1 which is 2,3,4,5-tetrahydro-3-phenyl-1H-[1,2,5]triazepino[1,2-a][1,2,4]benzotriazin-7(8H)-thione.

10. A compound of claim 1 which is 2,3,4,5-tetrahydro-7-(methylthio)-3-phenyl-1H-[1,2,5]triazepino[1,2-a][1,2,4]benzotriazine.

11. A compound of claim 1 which is 2,3,4,5-tetrahydro-3-(phenylmethyl)-1H-[1,2,5]triazepine[1,2-a][1,2,4]benzotriazin-7(8H)-one.

12. A compound of claim 1 which is 2,3,4,5-tetrahydro-3-(phenylmethyl)-1H-[1,2,5]triazepino[1,2-a][1,2,4]benzotriazin-7(8H)-thione.

13. A compound of claim 1 which is 2,3,4,5-tetrahydro-1H-[1,2,5]triazepino[1,2-a][1,2,4]benzotriazin-7(8H)-one.

* * * * *